United States Patent
Karlsson-Parra et al.

(10) Patent No.: US 9,492,529 B2
(45) Date of Patent: *Nov. 15, 2016

(54) METHOD FOR PRIMING OF T CELLS (75) Inventors: Alex Karlsson-Parra, Uppsala (SE);
Anna-Carin Wallgren, Uppsala (SE);
Bengt Andersson, Mölndal (SE)

(73) Assignee: IMMUNICUM AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/110,899

(22) PCT Filed: Apr. 12, 2012

(86) PCT No.: PCT/EP2012/056658
§ 371 (c)(1),
(2), (4) Date: Dec. 18, 2013

(87) PCT Pub. No.: WO2012/140127
PCT Pub. Date: Oct. 18, 2012

(65) Prior Publication Data
US 2014/0093538 A1   Apr. 3, 2014

Related U.S. Application Data

(60) Provisional application No. 61/474,892, filed on Apr. 13, 2011.

(51) Int. Cl.
*A61K 39/145* (2006.01)
*A61K 39/12* (2006.01)
*A61K 35/17* (2015.01)
*C12N 5/0783* (2010.01)
*A61K 39/00* (2006.01)

(52) U.S. Cl.
CPC .............. *A61K 39/145* (2013.01); *A61K 35/17* (2013.01); *A61K 39/12* (2013.01); *C12N 5/0636* (2013.01); *A61K 2039/5158* (2013.01); *C12N 2502/11* (2013.01); *C12N 2502/1121* (2013.01); *C12N 2710/16134* (2013.01); *C12N 2710/16234* (2013.01); *C12N 2760/16134* (2013.01)

(58) Field of Classification Search
None
See application file for complete search history.

(56) References Cited

U.S. PATENT DOCUMENTS 5,827,642 A    10/1998  Riddell et al.
6,274,378 B1    8/2001  Steinman et al.
6,821,778 B1   11/2004  Engleman et al.
9,211,321 B2   12/2015  Karlsson-Parra et al.

FOREIGN PATENT DOCUMENTS

EP   1712634 A1      10/2006
WO   2006/065495 A2   6/2006
WO   2009/034172 A1   3/2009
WO   2011/053223 A1   5/2011

OTHER PUBLICATIONS

Forsberg et al. Strategic use of an adenoviral vector for rapid and efficient ex vivo-generation of cytomegalovirus pp65-reactive cytolytic and helper T cells. Br J Haematol. Apr. 2008;141(2):188-99. Epub Feb. 26, 2008.*
Brestrich et al. Adoptive T-cell therapy of a lung transplanted patient with severe CMV disease and resistance to antiviral therapy. Am J Transplant. Jul. 2009:9(7)1679-84. Epub May 20, 2009.*
Comoli et al. Infusion of autologous Epstein-Barr virus (EBV)-specific cytotoxic T cells for prevention of EBV-related lymphoproliferative disorder in solid organ transplant recipients with evidence of active virus replication. Blood. Apr. 1, 2002;99(7):2592-8.*
Gervais et al. Selected allogeneic dendritic cells markedly enhance human tumour antigen-specific T cell response in vitro. Cancer Immunol Immunother. Nov. 2009;58(11):1831-41. Epub Mar. 28, 2009.*
Rao et al. Human Peripheral Blood Mononuclear Cells Exhibit Heterogeneous CD52 Expression Levels and Show Differential Sensitivity to Alemtuzumab Mediated Cytolysis. Plos 1, 2012, 7(6): 1-12.*
Medical Disctionary (http://medical-dictionary.thefreedictionary.com/sensitized+cell).*
Johansson et al. Triggering of Dendritic Cell Responses after Exposure to Activated, but Not Resting, Apoptotic PBMCs. The Journal of Immunology, 2007, 179: 1711-1720.*
Liu et al. Manipulation of MHC-I/TCR Interaction for Immune Therapy. Cellular & Molecular Immunology. 2008;5(3)171-182.*
Forsberg, Ole, et al., Strategic use of an adenoviral vector for rapid and efficient ex vivo-generation of cytomegalovirus pp65-reactive cytolytic and helper T cells, British Journal of Haematology, 141:188-199 (2008).
Gustafsson, Karin, et al., Recruitment and Activation of Natural Killer Cells In vitro by a Human Dendritic Cell Vaccine, Cancer Research, 68:5965-5971 (2008).
Wei, Joe, et al., Influenza A Infection Enhances Cross-Priming of CD8 + T Cells to Cell-Associated Antigens in a TLR7-and Type I IFN-Dependent Fashion, The Journal of Immunology, 185:6013-6022 (Oct. 2010).
Gervais, Alban, et al., Selected allogeneic dendritic cells markedly enhance human tumour antigen-specific T cell response in vitro, Cancer Immunol Immunother, 58:1831-1841 (2009).
Wallgren, A. C., et al., Direct Allorecognition Promotes Activation of Bystander Dendritic Cells and Licenses Them for Th1 Priming: A Functional Link Between Direct and Indirect Allosensitization, Scandinavian Journal of Immunology, 62:234-242 (2005).
Carlsson, Bjorn, et al., Simultaneous Generation of Cytomegalovirus-Specifi CD8+ and CD4+ T Lymphocytes by Use of Dendritic Cells Comodified with pp65 mRNA and pp65 Protein, The Journal of Infecious Diseases, 192:1912-1920 (2005).

(Continued)

*Primary Examiner* — Nick Zou
(74) *Attorney, Agent, or Firm* — Porter Wright Morris & Arthur LLP (57) ABSTRACT

The present invention relates to an in vitro method for priming T cells suitable for administration to a patient having a viral infection. The invention is also directed to the composition obtained by the method and uses thereof.

16 Claims, 10 Drawing Sheets

(56) References Cited

OTHER PUBLICATIONS

Carlsson, Bjorn, et al., Ex vivo stimulation of cytomegalovirus (CMV)-specific T cells using CMV pp65-modified dendritic cells as stimulators, British Journal of Haematology, 121:428-438 (2003).
Chuan, Jin, et al., A Protocol for Ex Vivo Expansion of Effector T Cells That Are Resistant to Oxidative and Apoptotic Stress, Molecular Therapy, vol. 20, Supp. 1, S263 Abstract 682, (May 2012).
Chang et al, Phase II Trial of Autologous Tumor Vaccination, Anti-CD3-Activated Vaccine-Primed Lymphocytes, and Interleukin-2 in Stage IV Renal Cell Cancer, Journal of Clinical Oncology, vol. 21, No. 5, pp. 884-890 (2003).
Decrion et al, A Subset of functional effector-memory CD8+ T lymphocytes in human immunodeficiency virus-infected patients, Immunology, 121:405-415 (2007).
Einsele et al, Infusion of cytomegalovirus (CMV)-specific T cells for the treatment of CMV infection not responding to antiviral chemotherapy, Blood, 99(11):3916-3922 (2002).
Gattinoni et al, Acquisition of full effector function in vitro paradoxically impairs the in vivo antitumor efficacy of adoptively transferred CD8+ T cells, The Journal of Clinical Investigation, vol. 115, No. 6, pp. 1616-1626, Jun. 2005.
Gritzapis et al, Identification of a Novel Immunogenic HLA-A*0201-Binding Epitope of HER-2/ neu with Potent Antitumor Properties, Journal of Immunology, 2008; 181: 146-154.
Ho et al, In vitro methods for generating CD8+ T-cell clones for immunotherapy from the naive repertoire, Journal of Immunological Methods, 310:40-52 (2006).
Jordan et al, Optimal analysis of composite cytokine responses during alloreactivity, Journal of Immunological Methods 260:1-14 (2002).
Mailliard et al, Alpha-Type-1 Polarized Dendritic Cells: A Novel Immunization Tool with Optimized CTL-inducing Activity, Cancer Research, 64:5934-5937 (2004).
Murphy et al, Gene Modification Strategies to Induce Tumor Immunity, Immunity, vol. 22, 403-414, 2005.
Ochsenbein et al, CD27 Expression Promotes Long-Term Survival of Functional Effector-Memory CD8+ Cytotoxic T Lymphocytes in HIV-infected Patients, J. Exp. Med, vol. 200, No. 11, pp. 1407-1417 (2004).
Powell, Jr et al, Transition of late-stage effector T cells to CD27+ CD28+ tumor-reactive effector memory T cells in humans after adoptive cell transfer therapy, Blood, vol. 105, No. 1, pp. 241-250 (2005).
Robbins et al, Cutting Edge: Persistence of Transferred Lymphocyte Clonotypes Correlates with Cancer Regression in Patients Receiving Cell Transfer Therapy, The Journal of Immunology 2004; 173:7125-7130.
Sadelain et al, Targeting Tumours With Genetically Enhanced T Lymphocytes, Nature Review/Cancer, 3:35-45 (2003).
Vera et al, Immunotherapy of Human Cancers Using Gene Modified T Lymphocytes, Curr Gene Ther. Oct. 2009; 9(5): 396-408.
Yang et al, A Simplified Method for the Clinical-scale Generation of Central Memory-like CD8+ T Cells After Transduction With Lentiviral Vectors Encoding Antitumor Antigen T-cell Receptors, J. Immunotherapy, vol. 33, No. 6, pp. 648-658, Jul.-Aug. 2010.
Stuber et al., Expression of interleukin-2 receptor on blood lymphocytes stimulated with allogeneic lymphocytes or autologous tumor cells, Cancer Immunol, 1990, v.31, pp. 76-80.
Tumeh et al., The impact of ex vivo clinical grade activation protocols on human T cell phenotype and function for the generation of genetically modified cells for adoptive cell transfer therapy, J Immunother, 33(8):759-768 (Oct. 2010).
Fu et al., A Simple and Sensitive Meethod for Measuring Tumor-Specific T Cell Cytotoxicity, PLoS ONE, vol. 5, Issue 7, e11867 (Jul. 29, 2010).
U.S. Office Action dated Dec. 30, 2015 from corresponding U.S. Appl. No. 14/110,901.

* cited by examiner

METHOD FOR PRIMING OF T CELLS

TECHNICAL FIELD

The present invention relates to the field of immunology and treatment of infectious diseases and more specifically to a method of activation of antigen specific T cells and the T cells produced by said method.

BACKGROUND

An increased understanding of the mechanisms by which T cells recognize virus and tumor-specific antigens has stimulated much interest in the use of specific T cells as adoptive immunotherapy for infections and malignant diseases. Cellular immunotherapy can be broadly defined as the administration of effector cells of the immune system for the treatment of disease. The primary function of the cellular immune system is to afford protection against pathogens, including acute and persistent infections.

T cells recognize infected cells and prevent onset of disease by killing these target cells. However, the interplay of pathogens and the immune system is complex, as demonstrated by chronic infections developing in the presence of specific T cells, whereby the pathogens obviously could evade T-cell surveillance.

The ability of T cells to detect virtually any pathogenic invader is granted by its extraordinarily diverse receptor repertoire, which allows the T-cell pool to recognize a vast number of peptides upon presentation by major histocompatibility complex (MHC) molecules. Still, signaling through the T-cell receptor (TCR) (signal 1) is not sufficient for adequate T-cell activation, as costimulatory molecules provide indispensable signals for proliferation, survival, and differentiation (signal 2). In fact, naive T cells that only receive signal 1 without signal 2 are rendered anergic (unresponsive) or die through apoptosis. The integration of signals 1 and 2 is required for full T-cell activation, and the strength of these signals shapes the size of the ensuing T-cell pool. Moreover, full differentiation into effector T cells is generally dependent on a third signal, which is supplied by the antigen-presenting cell (APC) in soluble form and provides instructive signals for the type of effector T cell that is required. This 'three-signal' concept depicts a model for the activation of naive T cells and the subsequent formation of effector T cells. Yet, the immune system provides a plethora of diverse costimulatory molecules and these various types of signal 2 and 3 all contribute in their own unique manner to the quality of the T-cell response. Costimulatory signals and soluble forms of signal 3 can act on particular aspects of T-cell activation, such as survival, cell cycle progression, type of effector cell to be developed, and differentiation to either effector or memory cell.

It is now generally accepted that mature antigen-presenting dendritic cells (DCs) have to be "helped" by other lymphocytes, including CD4+ T cells, NK cells and NKT cells, in order to induce long-lived memory CD8+ T cells. This "help" induces the mature DCs to differentiate further, a process known as licensing. "Helper" signals has multiple effects on DCs, including the upregulation of costimulatory molecules, the secretion of cytokines, and the upregulation of several antiapoptotic molecules, all of which cumulatively potentiate the ability of DCs to optimally activate cognate T cells, especially CD8+ T cells. Moreover, "helper" lymphocytes may also express or secrete factors that directly affect T cell survival, cell cycle progression, type of effector cell to be developed, and differentiation to either effector or memory cell.

Persistent or chronic viral infections, such as HIV, HBV, or HCV, or the herpes viruses CMV and EBV, present a significant threat to society, and treatment options for infected individuals are in urgent demand. During viral persistence, the balance between the virus and the host immune response is crucial. The immune system keeps the virus in check, and the virus counters by evading the immune response to avoid clearance, ultimately tipping the balance in favor of the virus and causing disease in many cases. In most persistent viral infections, the continuous presence of the viral antigen renders virus-specific T cells to become dysfunctional.

During the past 20 years, human immunodeficiency virus (HIV) infection has become a pandemic, with more than 40 million people infected and already more than 20 million deaths from acquired immunodeficiency syndrome (AIDS). Data from exposed uninfected and from long-term nonprogressors strongly suggest that both HIV-specific CD8+ and CD4+ T-cell functions are essential for protective immunity. HIV-specific CD8(+) T cells persist in high frequencies in HIV-infected patients despite impaired CD4(+) T helper response to the virus, but, unlike other differentiated effector cytotoxic T lymphocytes, most continue to express the tumor necrosis factor receptor family member CD27. The ligand for CD27 (CD70) is also overexpressed in HIV-infected hosts and the nature of expression and potential functional consequences of CD27 expression on HIV-specific CD8(+) T cells is therefore of interest. Analysis of CD27(+) and CD27(−) T cells derived from the same HIV-specific clone has revealed that retention of CD27 do not interfere with acquisition of effector functions, and that after T cell receptor stimulation, CD27(+) cells that concurrently are triggered via CD27 exhibit more resistance to apoptosis, interleukin 2 production, and proliferation than CD27(−) T cells. After transfer back into an HIV-infected patient, autologous HIV-specific CD27(−) T cells rapidly disappear, but CD27(+) T cells derived from the same clone persist at high frequency. It is therefore suggested that the CD27-CD70 interaction in HIV infection may provide CD27(+) CD8(+) T cells with a survival advantage and compensate for limiting or absent CD4(+) T help to maintain the CD8 response. (Ochsenbein et al., Exp Med. 2004 Dec. 6; 200(11):1407-17)

Similar to HIV, it has been found that also patients infected with persistent viral infections other than HIV have a subset of intermediate functional effector-memory T cells not fully differentiated but express not only CD28 but also CD27. It has been shown that these cells have a higher proliferative capacity than mature CD8+ T cells which are devoid of both CD28 and CD27. (Decrion et al., Immunology, 121, 405-415, 2007).

Thus, there is a strong correlation between the potency and specificity of the virus-specific CTL response and the magnitude of the viral load and the clinical outcome in most individuals infected with a chronic viral disease, the delay or arrest in disease progression in long-term nonprogressors, and the protection of some virus-exposed individuals from infection. It is likely that increasing the quality and breadth of the virus-specific CTL response would augment the control of virus replication in chronically infected individuals and either stabilize or improve their clinical course.

One strategy for fighting viral infections and increase the CTL response would therefore be adoptive T-cell therapy, which involves the transfer of effector T cells to restore specific T-cell responses in the host. Adoptive cell transfer therapy is the administration of ex vivo activated and expanded autologous virus-reactive T cells.

In present methods of adoptive immunotherapy of HIV patients problems with decline of transferred CTLs are pronounced. Although the decline in transferred CTLs in peripheral blood in part reflects migration to lymph node sites, the loss of antiviral activity over time indicates the CTLs die or are rendered dysfunctional at these local sites of HIV replication. Strategies to provide help to transferred CD8⁺ CTLs should improve CTL survival and elucidate the therapeutic potential of CTLs for controlling progression of HIV infection and also other viral infections.

Consequently, there is a need for an improved method of preparing a T cell population for use in adoptive immunotherapy against viral infections that increases proliferation and survival of antigen-specific T cells during their activation.

SUMMARY

The present invention relates to an in vitro method for priming of antigen specific CD4+ and/or CD8+ T cells suitable for administration to a patient having a viral infection. The method comprises co-culturing target T cells from the patient to be treated, dendritic cells, infectious material or infection associated proteins or peptides and lymphocytes. The lymphocytes are sensitized against MHC class I and/or MHC class II antigens on antigen presenting cells (APCs). The lymphocytes are sensitized by way of a mixed leukocyte reaction.

The present invention also relates to the antigen specific CD4+ and/or CD8+ T cells obtainable by the method and uses thereof.

DEFINITIONS

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

In the context of the present invention the term "antigen-specific" relates to the specific recognition/binding by a unique T cell receptor (TCR) of a short unique peptide sequence presented on a self MHC molecule.

In the context of the present invention the term "priming" and "activation" relates to a programmed activation process that occurs in a naive antigen-specific T cell that become stimulated by antigen-presenting cells with or without concurrent presence of "helper" cells.

In the context of the present invention the term "responder cells" relates to different lymphocyte subpopulations, including, but not limited to, T cells, NK cells and NKT cells which respond to co-cultured allogeneic PMBCs by activation and/or proliferation.

In the context of the present invention the term "sensitized cells" relates to different lymphocyte subpopulations, including T cells, NK cells and NKT cells which have been pre-activated by co-cultured allogeneic cells, including PBMCs.

In the context of the present invention the term "target cells" relates to CD4+ or CD8+ T cells that become stimulated by either allogeneic or autologous APCs or antigen-presenting autologous APCs. Sites of patient lymphocyte (target cell) collection can, for example, be peripheral blood or bone marrow.

In the context of the present invention the term "mature" in relation to monocyte-derived DCs relates to their expression of "maturity-markers", including, but not limited to, CD40, CD86, CD83 and CCR7 that is induced by the stimulation of immature DCs with microbial products such as LPS or inflammatory mediators such as TNF-alpha and/or IL-1 beta.

Immature DCs are cells characterized by high endocytic activity and low T-cell activation potential. Immature DCs constantly sample the surrounding environment for pathogens such as viruses and bacteria. Immature DCs phagocytose pathogens and degrade their proteins into small pieces and upon maturation present those fragments at their cell surface using MHC molecules. Simultaneously, they upregulate cell-surface receptors that act as co-receptors in T-cell activation such as CD80, CD86, and CD40 greatly enhancing their ability to activate T-cells. They also upregulate CCR7, a chemotactic receptor that induces the dendritic cell to travel through the blood stream to the spleen or through the lymphatic system to a lymph node. Here they act as antigen-presenting cells: they activate helper T-cells and killer T-cells as well as B-cells by presenting them with antigens derived from the pathogen, alongside non-antigen specific costimulatory signals. Mature DCs probably arise from monocytes, white blood cells which circulate in the body and, depending on the right signal, can turn into either DCs or macrophages. The monocytes in turn are formed from stem cells in the bone marrow. Monocyte-derived DCs can be generated in vitro from peripheral blood monocytes.

In the context of the present invention the term "non-proliferative" of a cell is used to indicate that the cell has been rendered incapable of cell division to form progeny. The cell may nonetheless be capable of response to stimulus, or biosynthesis and/or secretion of cell products such as cytokines. Methods of making cells non-proliferative are known in the art. Preferred methods of making cells non-proliferative are treatment with anti-proliferative drugs such as mitomycin C, or irradiation, such as gamma irradiation. Cells that have been fixed or permeabilized and are incapable of division are also examples of non-proliferative cells.

In the context of the present invention the term "mixed lymphocyte reaction", mixed lymphocyte culture", "MLR", and MLC are used interchangeably to refer to a mixture comprising a minimum of two different cell populations that are allotypically different. At least one of the allotypically different cells is a lymphocyte. The cells are cultured together for a time and under suitable conditions to result in the stimulation of the lymphocytes. A frequent objective of an MLR is to provide allogeneic stimulation such as may initiate proliferation of the lymphocytes; but unless indicated, proliferation during the culture is not required. In the proper context, these terms may alternatively refer to a mixture of cells derived from such a culture.

As used herein, the term "treatment" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, and diminishment of any direct or indirect pathological consequences of the disease, lowering the rate of disease progression, amelioration or palliation of the disease state, and remission or improved prognosis.

The term "antigen-presenting cells (s)", "APC" or "APCs" etc comprise PBMCs, monocytes, B-cells or monocyte-derived DCs from the patient to be treated or from an unrelated blood donor expressing at least one MHC class II antigen that is identical with MHC class II antigens expressed on APCs from the patient to be treated.

In the context of the present invention a "chronic infection" is a long lasting persistent infection that evades the immune system of its host. A chronic infection can be caused by a bacteria or a virus. Non-limiting examples of viruses causing chronic infections are human immunodeficiency virus (HIV), hepatitis B virus (HBV), hepatitis C virus (HCV), cytomegalovirus (CMV) and Epstein-Barr virus (EBV).

In the context of the present invention the term "culturing" refers to the in vitro propagation of cells or organisms in media of various kinds. It is understood that the descendants of a cell grown in culture may not be completely identical (morphologically, genetically, or phenotypically) to the parent cell. A suitable culturing medium can be selected by the person skilled in the art and examples of such media are RPMI medium or Eagles Minimal Essential Medium (EMEM).

The terms "major histocompatibility complex" and "MHC" refer to a complex of genes encoding cell-surface molecules that are required for antigen presentation to T cells and for rapid graft rejection. In humans, the MHC complex is also known as the HLA complex. The proteins encoded by the MHC complex are known as "MHC molecules" and are classified into class I and class II MHC molecules. Class I MHC molecules include membrane heterodimeric proteins made up of a chain encoded in the MHC associated non-covalently with β2-microglobulin. Class I MHC molecules are expressed by nearly all nucleated cells and have been shown to function in antigen presentation to CD8+ T cells. Class I molecules include HLA-A, -B, and -C in humans. Class I molecules generally bind peptides 8-10 amino acids in length. Class II MHC molecules also include membrane heterodimeric proteins.

Class II MHCs are known to participate in antigen presentation to CD4+ T cells and, in humans, include HLA-DP, -DQ, and DR. Class II molecules generally bind peptides 12-20 amino acid residues in length. The term "MHC restriction" refers to a characteristic of T cells that permits them to recognize antigen only after it is processed and the resulting antigenic peptides are displayed in association with either a self class I or self class 11 MHC molecule.

The terms "vaccine", "immunogen", or immunogenic composition" are used herein to refer to a compound or composition that is capable of conferring a degree of specific immunity when administered to a human or animal subject. As used in this disclosure, a "cellular vaccine" or "cellular immunogen" refers to a composition comprising at least one cell population, which is optionally inactivated, as an active ingredient. The immunogens, and immunogenic compositions of this invention are active, which mean that they are capable of stimulating a specific immunological response (such as an anti-virus antigen or anti-virus response) mediated at least in part by the immune system of the host. The immunological response may comprise antibodies, immunoreactive cells (such as helper/inducer or cytotoxic cells), or any combination thereof, and is preferably directed towards an antigen that is present on a virus towards which the treatment is directed. The response may be elicited or restimulated in a subject by administration of either single or multiple doses.

A compound or composition is "immunogenic" if it is capable of either: a) generating an immune response against an antigen (such as a viral antigen) in a naive individual; or b) reconstituting, boosting, or maintaining an immune response in an individual beyond what would occur if the compound or composition was not administered. A composition is immunogenic if it is capable of attaining either of these criteria when administered in single or multiple doses.

Description

The present invention relates to the production of allo-sensitized allogeneic lymphocytes (ASALs) to promote increased proliferation and survival of antigen-specific T cells during their activation by antigen-presenting cells, including dendritic cells (DCs).

The present invention is based on in vitro studies using peripheral blood mononucelar cells (PBMCs), and subpopulations thereof, from human healthy blood donors where a positive regulatory role for ASALs in the induction of antigen-specific human CD8+ T cell responses was demonstrated. Using an allogeneic in vitro model, tracking proliferation and survival of alloreactive CD8+ T cells in the presence of ASALs, the proliferative capacity after re-stimulation was increased more that 5-fold and apoptotic cell death reduced from 10 to 5%.

Addition of ASALs leads to a strongly upregulated expression of the costimulatory molecule CD70 on antigen-presenting DCs and to production of IL-12 and IFN-gamma, two factors with a well-known positive impact on T cell commitment into type 1 CD4+ and CD8+ T cells. Further, addition of ASALs also led to production of IL-2, a well-known growth factor for T cells. Notably, CD70-mediated interactions have recently been shown to promote survival of activated T cells throughout successive rounds of division and thereby contribute to the accumulation of effector T cells.

The present invention relates to an in vitro method for priming of antigen specific CD4+ and/or CD8+ T cells suitable for administration to a patient having a viral infection. The method comprises co-culturing target T cells from the patient to be treated with DCs, preferably monocyte-derived DCs, autologous or allogeneic infectious material or infection associated proteins or peptides and lymphocytes sensitized against MHC class I and/or MHC class II antigens on antigen presenting cells (APCs). Said APCs preferably being allogeneic with respect to the lymphocytes. The DCs may be autologous or allogeneic.

The present invention also provides a method of preparing a T cell population for use in adoptive immunotherapy comprising T cells engineered (by viral transduction, transfection, electroporation or other methods of introducing genetic material) to express a T cell receptor or a chimeric T cell receptor that recognize the target antigen; activating these engineered T cells with antigen-loaded DCs in the presence of anti-CD3 antibodies and sensitized lymphocytes; expanding these target cells in culture; and reintroducing these cells back into the patient. More specifically, an in vitro method for priming of antigen specific CD4+ and/or CD8+ T cells suitable for administration to a patient having a viral infection wherein the CD4+ and/or CD8+ T cells have been genetically manipulated. The method comprises co-culturing viral antigen receptor transfected target T cells from the patient to be treated with DCs (preferably monocytes-derived), anti-CD3 antibodies and lymphocytes sensitized against MHC class I and/or MHC class II antigens on antigen presenting cells (APCs).

Target T cells can be transformed with T cell receptor (TCR) coding genes or alternatively through the use of a chimeric antigen receptor (CAR) that is capable of relaying excitatory signals to T cells in a non-MHC-restricted manner. These hybrid proteins, composed of an extracellular antigen recognition domain fused to an intracellular T-cell activation domain, may therefore be used in patients regardless of their human leukocyte antigen genotype. Prior to transfection, the target T cells are preferably pre-stimulated with anti-CD3 antibodies in order to optimize subsequent transduction. Any suitable CAR can be used in the present invention. The CAR ligand should be expressed by the virus. Selecting and preparing a suitable CAR is within the skills of the person skilled in the art.

Transduction of TCR- or CAR-coding genes into T cells can be performed by using any suitable method known to the skilled person, such as viral or non viral vectors (see for example Sambrook et al., Molecular Cloning, A Laboratory Manual, 3rd ed., vol. 1-3, Cold. Spring Harbor Laboratory, Cold Spring Harbor, N.Y.). Non-limiting examples of viral vectors include retro, lenti, adeno, adeno-associated viral vectors and non-limiting non-viral vector systems include electrotransfer of plasmids and transposon/transposase systems.

Lymphocytes from the patient that are to be expanded may originate from the peripheral blood or the bone marrow.

The viral infection may be a chronic viral infection. Non-limiting examples of viruses causing a chronic viral infection are HIV, HBV, HCV, CMV and EBV. Patients having a chronic viral infection have inactive virus specific CTLs and are therefore a suitable target for the inventive method priming antigen specific Th1 cells or CTLs. Inactive HIV specific CTLs are present in HIV patients in a high concentration. The inactive CTLs express the CD 70 receptor, CD27, in a high degree making the primed antigen specific Th1 cells or CTLs of the present invention particularly suitable for administration to HIV patients.

The ASALs are responder cells obtained from a mixed leukocyte reaction that are cultured together with DCs and target cells. When the target T cells are genetically manipulated, also anti-CD3 antibodies are added to the culture. The ASALs are selected from the group consisting of peripheral blood lymphocytes, including $CD4^+$ T cells, $CD8^+$ T cells and natural killer (NK) cells. The target cells are $CD4^+$ and/or $CD8^+$ T cells that preferably are autologous to the DCs and the DCs are preferably monocytes-derived. The monocyte-derived DCs are loaded with virus material or virus associated proteins or peptides or virus derived antigens.

Addition of ASALs further leads to an enrichment for a population of target CD8+ T cells expressing high levels of CD27. $CD27^+$ $CD8^+$ T cells represent potentially more effective CTLs (cytotoxic T cells) for adoptive immunotherapy since they can provide an antigen-driven autocrine signal for proliferation. Such helper-independent CD8 T cells would not require exogenous help in the form of IL-2 or CD4+ T cells to survive and expand. Thus, the present invention provides methods for treating an immune-mediated disease by providing a subject with a CD8+ T cell population that is programmed for strong cytotoxic activity in the absence or reduced presence of additional cytokines, such as IL-2, or CD4+ T cells. The methods are particularly useful for ex vivo expansion of cytolytic, virus-specific CD8+ T cells, but may also be used for expansion of virus-specific CD4+ T cells.

The percentage of cytolytic antigen-specific CD8+ T cells expressed as percentage of the total number of CD8+ T lymphocytes is preferably at least about 5%, more preferably at least about 10%, more preferably at least about 15%, more preferably at least about 20%, even more preferably at least about 25%, even more preferably at least about 30% and most preferably at least about 35%.

More specifically, the method of the present invention relates to an in vitro method for priming of antigen specific CD4+ and/or CD8+ T cells suitable for administration to a patient having a viral infection, wherein said method comprising the following steps:
a) culturing non-proliferating antigen presenting cells together with peripheral blood mononuclear cells that are allogeneic with respect to the non-proliferating antigen presenting cells,
b) culturing monocytes in a composition allowing the monocytes to mature to mature DCs (the composition is further described below), and
c) culturing lymphocytes, including but not limited to CD4+ T cells, CD8+ T cells and/or natural killer (NK) cells from step a) with mature DCs from step b).

The monocyte-derived DCs are obtained by first culturing monocytes in a composition comprising GM-CSF and IL-4 for about 2-7 days, preferably about 5 days to obtain immature DCs and subsequently add a second composition that enables the immature DCs to become mature DCs by culturing for at least about 12 to 72 hours and preferably about 24-48 hours. The second composition comprises components that allow the immature DCs to become mature monocyte-derived DCs that can be used to activate CD4+ and CD8+ T cells. In one embodiment the second composition comprises TNF alfa, IL-1 beta, interferon gamma, interferon beta and a TLR3 ligand, such as poly-l:C (Mailliard et al., Alpha-type-1 polarized DCs: a novel immunization tool with optimized CTL-inducing activity. *Cancer Res.* 2004; 64:5934-5937.). In another embodiment the second composition comprises interferon gamma, a TLR 3 and/or a TLR 4 ligand and a TLR7 and/or a TLR 8 ligand and/or a TLR9. ligand. Non-limiting examples of a TLR 3 ligand is poly-l:C, of a TLR7/8 ligand is R848, and of a TLR9 ligand is CpG.

The sensitization of allogeneic lymphocytes is induced by a traditional mixed leukocyte reaction (MLR or MLC-mixed leukocyte culture) comprising culturing inactivated antigen presenting cells with peripheral blood mononuclear cells (PBMCs) that are allogeneic with respect to the antigen presenting cells. The performance of an MLR is well known to the skilled person (Jordan W J, Ritter M A. Optimal analysis of composite cytokine responses during alloreactivity. *J Immunol Methods* 2002; 260: 1-14). In an MLR peripheral blood lymphocytes from two individuals are mixed together in tissue culture for several days. Lymphocytes from incompatible individuals will stimulate each other to proliferate significantly (measured for example by tritiated thymidine uptake) whereas those from compatible individuals will not. In a one-way MLC, the lymphocytes from one of the individuals are inactivated (usually by treatment with toxins, such as mitomycin or irradiation, such as gamma irradiation) thereby allowing only the untreated remaining population of cells to proliferate in response to foreign histocompatibility antigens.

The antigen presenting cells used in the MLR are selected from the group consisting of PBMCs and monocytes-derived DCs. The monocytes-derived DCs are from the patient or from a healthy donor, i.e. can be autologous or allogeneic.

The infectious material or infection associated proteins or peptides are selected from the group consisting of killed viral particles from the patient, allogeneic viral particles of the same type as the viral infection of the patient and isolated and purified viral proteins or peptides. Isolated and purified viral proteins or peptides are well known to the skilled person. In one embodiment the viral material is viral proteins loaded into the monocytes-derived DCs by transfection with mRNA encoding the viral protein.

In the method of the present invention the cells (T cells from the patient to be treated, monocyte-derived dendritic cells, virus material or virus associated proteins or peptides and lymphocytes sensitized against MHC class I and/or MHC class II antigens on antigen presenting cells (APCs) that are allogeneic with respect to the lymphocytes) are co-cultured for at least about 20 days, preferably for about 6 to 20 days and more preferably about 8 to 14 days.

In one embodiment of the inventive method anti-CD3 antibodies, exogenous IL-2, IL-7, IL-15, anti-IL-4 and/or IL-21 are added to the cell culture in order to optimize cell proliferation and survival.

It is also possible to restimulate the primed antigen specific CD4+ and/or CD8+ T cells by culturing said cells together with new DCs, new sensitized lymphocytes and optionally addition of anti-CD3 antibodies and/or exogenous IL-2, IL-7, IL-15, anti-IL-4 and/or IL-21 to the cell culture.

The present invention also relates to an immunogenic composition obtainable by the method described above as well as the antigen specific CD4+ and/or CD8+ T cells obtainable by the method described above.

The antigen specific CD4+ and/or CD8+ T cells are suitable for administration to a patient and preferably have at least one of the following features:
  ability to proliferate without quickly reaching apoptosis
  express low levels of the apoptosis marker Annexin-V
  express CD27 and/or CD28 at their cell surface The present invention also relates to the antigen specific CD4+ and/or CD8+ T cells obtained by the inventive method for use as a medicament as well as for use in the manufacture of a medicament.

Further, the present invention relates to the use of antigen specific CD4+ and/or CD8+ T cells obtainable by the method of the invention or as defined above for use in the treatment of a viral infection, such as a chronic viral infection, or for eliciting an anti-infectious immunological response in a human as well as for the manufacture of a medicament for the treatment of a viral infection, such as a chronic viral infection, or for eliciting an anti-viral immunological response in a human. The CD4+ and/or CD8+ T cells can be administered after the first stimulation or alternatively after restimulation. In one embodiment the CD4+ and/or CD8+ T cells are administered in combination with a therapeutic anti-viral vaccine.

Methods of using T cell populations for adoptive cell therapy in treatment of human subjects are known to clinicians skilled in the art. T cell populations prepared according to the methods described herein and known in the art can be used in such methods. For example, adoptive cell therapy using CMV-specific T cells for the treatment of CMV infection (Einsele et al, Blood; 2002 (99) 3916-3922) and HIV-specific CD8+ T cells in HIV-infected patients (Ochsenbein et al., J. Exp. Med.; 2004(200) 1407-1417).

Antigen-primed T cells undergo increased proliferation and decreased apoptosis upon re-stimulation when exposed to ASALs during their initial DC-mediated priming in vitro. Thus, methods for enhancing secondary T cell responses upon vaccination if adoptively transferred back to the patient before and/or during vaccination are also contemplated by the present invention.

The present invention also provides methods for improving viral vaccine therapy. Many virus express foreign antigens that can potentially serve as targets for destruction by the immune system. Viral vaccines generate a systemic virus-specific immune response in a subject that comprises both humoral and cellular components. The response is elicited from the subject's own immune system by administering a vaccine composition subcutaneously, intramuscularly or per-orally. The antibodies or immune cells bind the virus antigen and lyse the viruses. However, there remains a need for increased T cell-responsiveness upon vaccination of patients afflicted with a viral infection. Adoptive transfer of preactivated apoptosis-resistant virus-specific T cells with high proliferative potential before, or at the time of vaccination, may therefore enhance vaccine-mediated immune responses in vivo.

The composition according to the invention can also be administered in combination with a therapeutic anti-viral vaccine.

The cells obtainable by the method of the invention can be administered directly to an organism, such as a human, to increase proliferation and survival of antigen-specific T cells during their activation. Administration of these cells, often with pharmaceutically acceptable carriers, is by any of the routes normally used for introducing a cell into ultimate contact with a mammal's blood or tissue cells.

Formulations suitable for parenteral administration, such as, for example, by intravenous, intramuscular, intradermal, intraperitoneal, and subcutaneous routes and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intravenous administration is the preferred method of administration for the CD4+ and/or CD8+ T cells of the invention.

The dose of the CD4+ and/or CD8+ T cells administered to a patient, in the context of the present invention should be sufficient to enhance the immune response in the patient. Thus, cells are administered to a patient in an amount sufficient to elicit an effective immune response to the virus antigen and/or to alleviate, reduce, cure or at least partially arrest symptoms and/or complications from the disease. An amount adequate to accomplish this is defined as a "therapeutically effective dose". The dose will be determined by the activity of the cells produced and the condition of the patient, as well as the body weight or surface area of the patient to be treated. In determining the effective amount of the cell to be administered in the treatment or prophylaxis of the disease, the physician needs to evaluate progression of the disease and the induction of immune response against any relevant virus antigen.

Encompassed by the present invention is any combination of the above disclosed embodiments.

The invention is further illustrated by the following non-limiting examples.

EXAMPLES

Example 1

Expression of CD 70

Material & Methods. Allosensitized allogeneic lymphocytes were generated in a standard one-way mixed leukocyte reaction (MLR) by co-culturing gamma irradiated PBMC from a healthy blood donor with non-irradiated PBMCs from an allogeneic donor (with respect to the healthy blood donor) at a ratio of 1:1 in serum-free X-VIVO 15 medium in tissue culture flasks for 5-7 days. For propagation of immature DCs, peripheral blood mononuclear cells (PBMCs) obtained from healthy blood donors were isolated on density gradients (Lymphoprep, Nycomed, Oslo, Norway). Isolated PBMCs were resuspended in AIM-V medium (Invitrogen, Paisley, UK), plated in 24-well plastic culture plates at $2.5 \times 10^6$ cells per well and allowed to adhere for 2 hours. Non-adherent cells were removed and the remaining adherent monocytes, were cultured in AIM-V medium supplemented with recombinant human GM-CSF and IL-4 (R&D Systems, Abingdon, UK; both at 1,000 U/mL) for 4-6 days. Maturation of immature DC was induced by supplementing the culture media with IFN-α (3,000 U/mL), IFN-γ (1,000 U/mL), TNF-α (50 ng/mL), IL-1β (25 ng/mL) (all from R&D Systems) and p-I:C (Sigma-Aldrich; 20 µg/mL) during the last 24 hours of incubation.

The mature DC populations all contained more than 70% CD83+DCs as determined by FACS analysis.

After washing, mature DCs were cocultured with allosensitized non-irradiated or gamma-irradiated (25 Grey) allogeneic lymphocytes in X-VIVO 15 medium for 24 h and analysed by FACS. Sensitization of alloreactive lymphocytes was performed by conducting a primary one-way MLR in serum-free culture media (X-VIVO 15) for 5-6 days with gamma-irradiated PBMCs as stimulator cells and non-irradiated PBMCs as responder cells. PE-conjugated anti-human CD70 was used for FACS studies.

Figure 1:
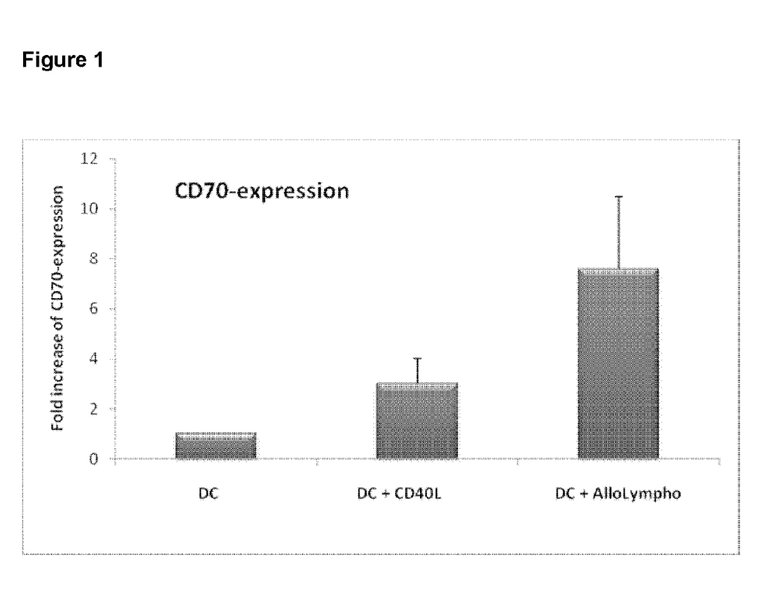
FIG. 1 illustrates that lymphocytes that have been sensitized against MHC antigens expressed on irradiated allogeneic peripheral blood mononuclear cells (PBMCs) in a conventional MLR markedly enhance the expression of CD70 on mature monocyte-derived DCs which are autologous to the irradiated PBMCs that were used as stimulator cells during the initial sensitizing MLR.

Results. As shown in FIG. 1, allogeneic lymphocytes that have been primed in a conventional MLR against irradiated PBMCs (allo-sensitized allogeneic lymphocytes, ASALs) markedly enhance the expression of CD70 on mature monocyte-derived DCs which are autologous to the irradiated PBMCs used in the MLR.

Figure 2:
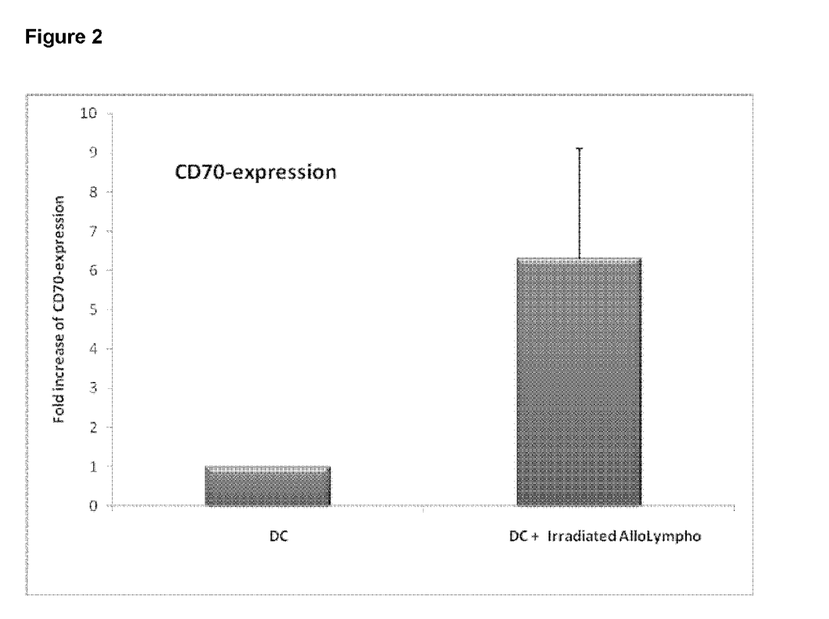
FIG. 2 illustrates that gamma-irradiated lymphocytes that have been sensitized against MHC antigens expressed on irradiated allogeneic PBMCs in a conventional MLR markedly enhance the expression of CD70 on mature monocyte-derived DCs which are autologous to the irradiated PBMCs that were used as stimulator cells during the initial sensitizing MLR.

As shown in FIG. 2, gamma-irradiated allogeneic lymphocytes similarly enhance the expression of CD70.

Figure 3:
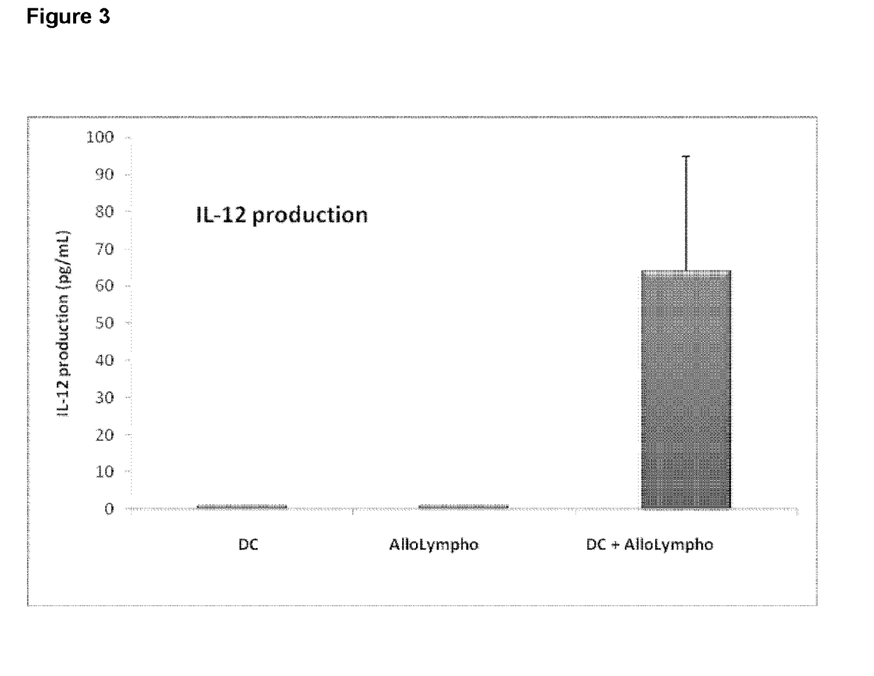
FIG. 3 illustrates that coculture of lymphocytes that have been sensitized against MHC antigens expressed on irradiated allogeneic PBMCs in a conventional MLR for 6 days with monocyte-derived DCs which are autologous to the irradiated PBMCs that were used as stimulator cells during the initial sensitizing MLR induce substantial IL-12 production.
Figure 4:
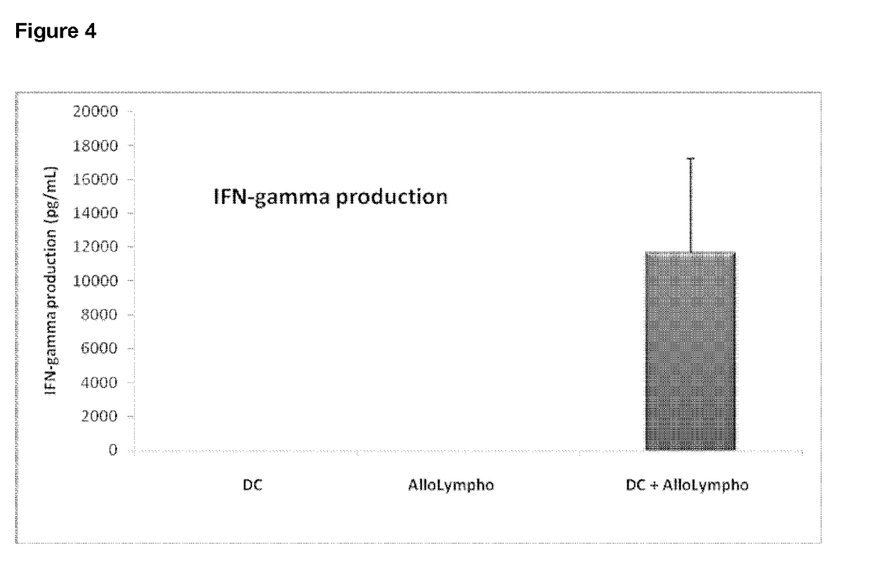
FIG. 4 illustrates that co-culture of lymphocytes that have been sensitized against MHC antigens expressed on irradiated allogeneic PBMCs in a conventional MLR for 6 days with monocyte-derived DCs which are autologous to the irradiated PBMCs that were used as stimulator cells during the initial sensitizing MLR induce substantial IFN-gamma production.
Figure 5:
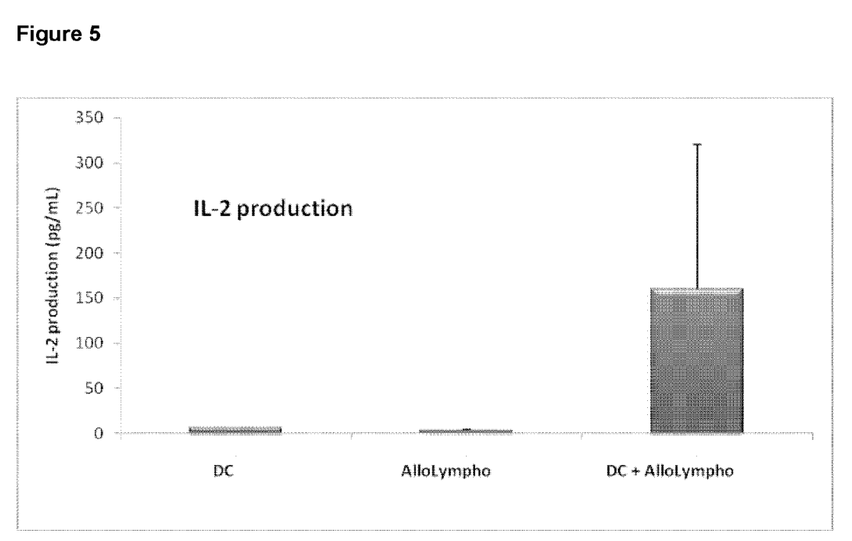
FIG. 5 illustrates that co-culture of lymphocytes that have been sensitized against MHC antigens expressed on irradiated allogeneic PBMCs in a conventional MLR for 6 days with monocyte-derived DCs which are autologous to the irradiated PBMCs that were used as stimulator cells during the initial sensitizing MLR induce substantial IL-2 production.

As shown in FIGS. 3, 4 and 5, coculture of mature DCs with sensitized allogeneic lymphocytes induce a substantial production of IL-12, IFN-gamma and IL-2

Example 2

Material and methods: See M&M in example 1.

CD8+ lymphocytes were isolated (using negative selection with antibody-coated magnetic beads) after coculture of DCs, irradiated allosensitized lymphocytes and PBMCs (allogeneic to the DCs) for 6 days and subsequently restimulated with B-cells (autologous to the DCs used during primary stimulation) and stained for expression of CD27 and Annexin-V. Subsequent analysis was performed with FACS.

Figure 6:
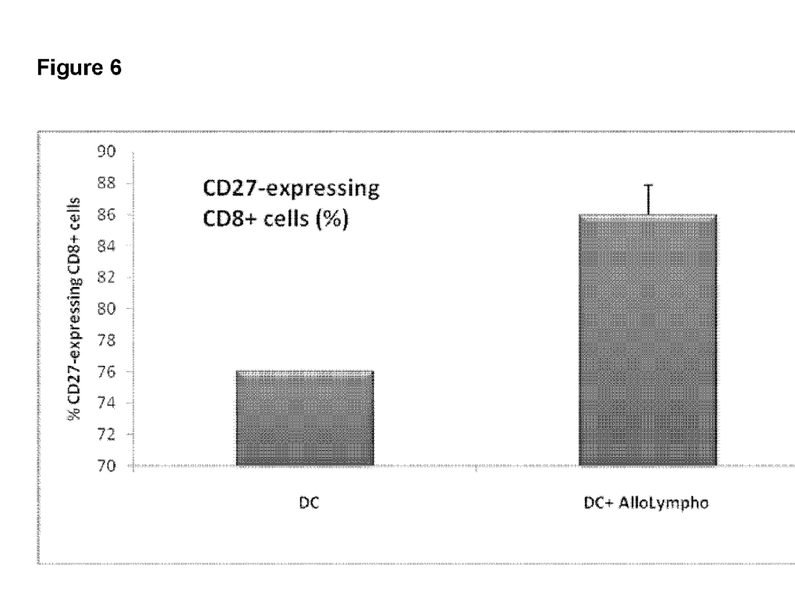
FIG. 6 illustrates that co-culture of a) irradiated lymphocytes that have been sensitized against MHC antigens expressed on irradiated allogeneic PBMCs in a conventional MLR with b) monocyte-derived DCs which are autologous to the irradiated PBMCs that were used as stimulator cells during the initial sensitizing MLR, induce a higher number of CD27-expressing alloreactive CD8+ T cells from a third-party donor.

Results:

As shown in FIG. 6, addition of allosensitized lymphocytes during primary stimulation substantially increased expression of CD27 when the CD8+ cells were restimulated with B-cells.

Figure 7:
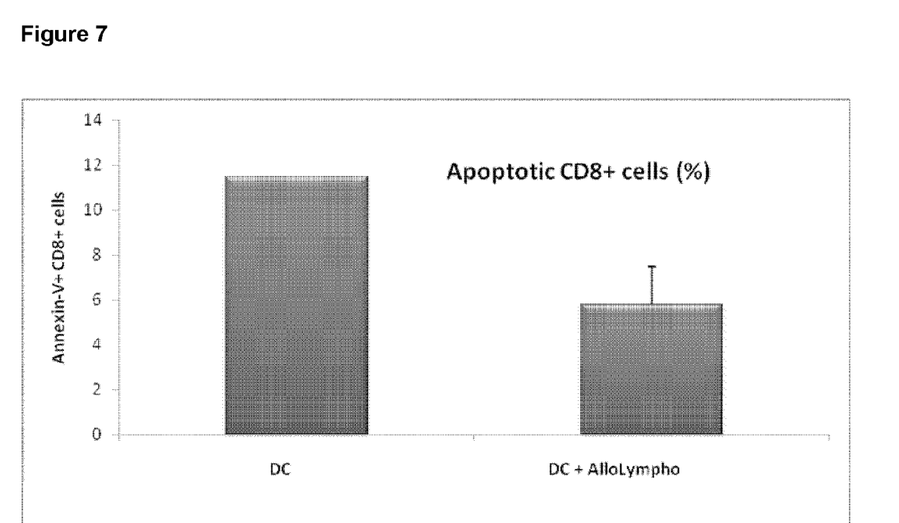
FIG. 7 illustrates that addition of irradiated lymphocytes that have been sensitized against MHC antigens expressed on irradiated allogeneic PBMCs in a conventional MLR to monocyte-derived DCs which are autologous to the irradiated PBMCs that were used as stimulator cells during the initial sensitizing MLR, reduces the number of apoptotic (Annexin-V positive) alloreactive CD8+ T cells from a third-party donor.

Addition of allosensitized lymphocytes during primary stimulation substantially reduced expression of Annexin-V (apoptosis marker) when the CD8+ cells were restimulated with B-cells (see FIG. 7).

Example 3

Material and methods: See M&M in example 2.

Before restimulation with B-cells the primed and isolated CD8+ cells were pulsed with 3H-Thymidine.

Figure 8:
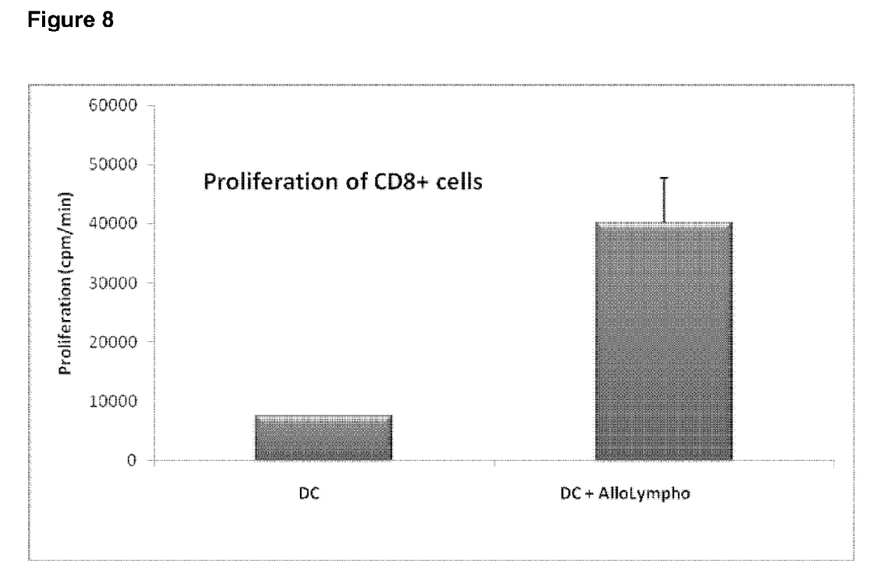
FIG. 8 illustrates that addition of irradiated lymphocytes that have been sensitized against MHC antigens expressed on irradiated allogeneic PBMCs in a conventional MLR to monocyte-derived DCs which are autologous to the irradiated PBMCs that were used as stimulator cells during the initial sensitizing MLR, induce a stronger (6-fold) secondary proliferative response in alloreactive CD8+ lymphocytes that are re-stimulated with B-cells that are autologous to the DCs used during primary stimulation.

Results:

As shown in FIG. 8, addition of allosensitized lymphocytes during primary stimulation strongly increased the proliferative response (as measured by incorporation of 3H-Thymidine, cpm/min, day 3) of CD8+ cells after restimulation.

Example 4

Material and methods: See M&M in example 3.

After coculture of B-cells and pre-activated CD8+ cells for 2 days culture supernatant was collected and analyzed for IFN-gamma production by a conventional ELISA (R&D Systems).

Figure 9:
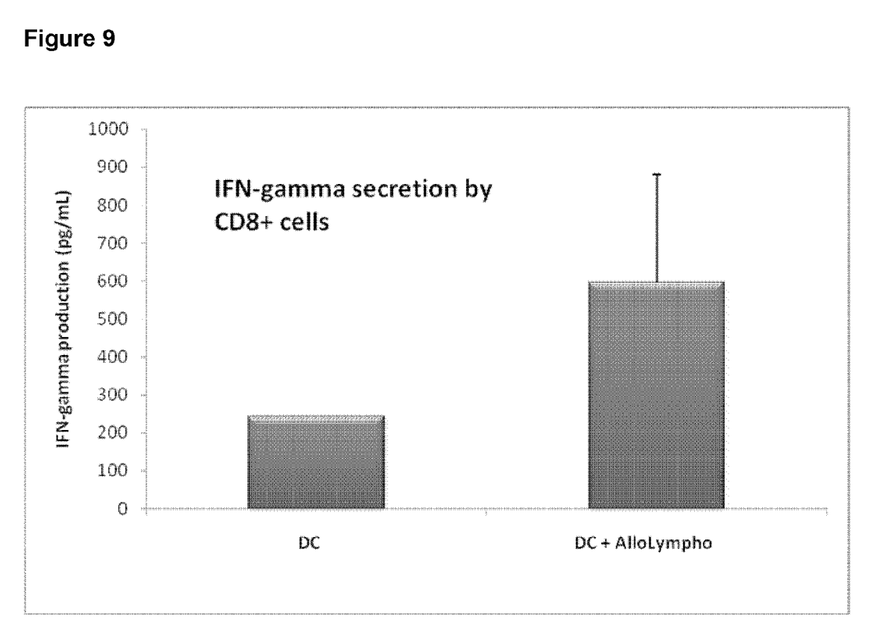
FIG. 9 illustrates that addition of irradiated lymphocytes that have been sensitized against MHC antigens expressed on irradiated allogeneic PBMCs in a conventional MLR to monocyte-derived DCs which are autologous to the irradiated PBMCs that were used as stimulator cells during the initial sensitizing MLR, induce a modest (3-fold) increase of IFN-gamma production by alloreactive CD8+ lymphocytes that are re-stimulated with B-cells that are autologous to the DCs used during primary stimulation.

Results:

FIG. 9 shows that addition of allosensitized lymphocytes during primary stimulation substantially increased production of IFN-gamma by CD8+ cells after restimulation.

Example 5

ASALs Increase the Frequency of Antigen-Specific CD8+ T Cells Generated Following Primary In Vitro Stimulation Materials & Methods: Peripheral blood mononuclear cells (PBMC) from healthy blood donors were isolated using a density medium and typed for HLA-A2 with monoclonal antibodies and flow cytometry, according to standard procedures, and frozen. After thawing PBMC were incubated in plastic wells to enrich monocytes by plastic adherence and after rinsing off the non-adherent cells incubation was performed in a cell culture medium containing GM-CSF and IL-4 for 5 days. Then the immature DC were incubated with a cytokine cocktail (containing IL-1β, TNF-α, IFN-α, and INF-γ) and a mix of overlapping MHC class I-binding peptides of antigens from CMV, EBV and influenza A-virus (PX14 ProMix CEF pool (standard); a peptide library from Proimmune LTD, Oxford, UK. The use of this mix is not limited to one HLA type.) for 48 hours (maturation of DC and pulsing with antigenic peptides).

In parallel activated allogeneic PBMC were produced in a mixed leucocyte reaction; MLR; with PBMC from a different blood donor. On day 7 a new batch of PBMC was thawed and was expanded with the pulsed DC and the activated allogeneic PBMC as described above for 7 days. The cells were then incubated for 7 days in cell culture medium containing IL-2 to make the T cell receptors reappear on the cell surface (during activation the T cells internalize their receptors). Then the cells were re-stimulated with pulsed DC (as described above) and after 1 hour a pentamer staining was performed, and after 24 hours an assay for IFN-γ-forming cells (ELISpot PLUS for Human Interferon-γ, Mabtech, Stockholm, Sweden) was performed according to instructions by the manufacturer. The number of virus-specific cells was measured as IFN-γ-spots per $10^6$ cells added. Phycoerythrin-conjugated pentamers A*02:01—NLVPMVATV for CMV, A*02:01—GLCTLVAML for EBV and A*02:01—NLVPMVATV for influenza A virus (all from Proimmune Ltd) were added and after incubation in the dark, at room temperature for 10 minutes, monoclonal antibodies to CD3 and CD8 (from BD Biosciences, San José, Calif., USA) were added. After incubation in the dark for 20 minutes on ice, the cells were analysed in a flow cytometer (FACSCanto using the FACDdiva software, BD Biosciences). The frequencies of virus-specific T-cells were expressed as % of CD8-positive cells.

Figure 10:
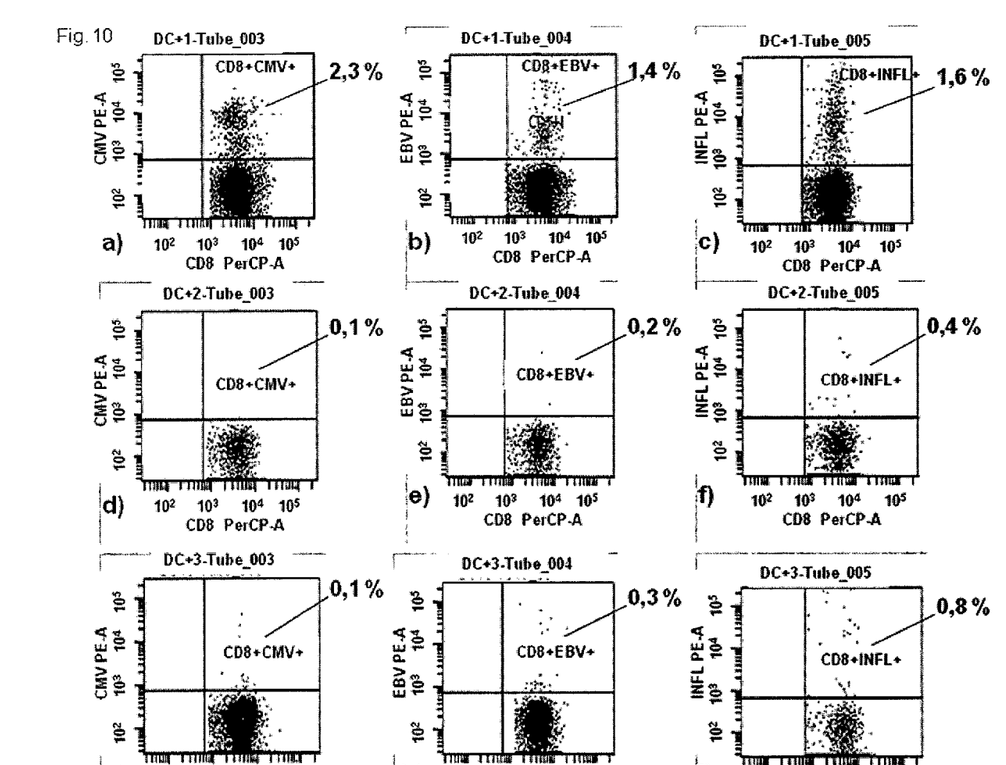
FIG. 10 illustrates the frequencies of virus-specific CD8 positive cells (specific for CMV, EBV or influenza A virus respectively) after expansion with a) activated allogeneic cells and antigen-loaded (a, b and c), expansion with antigen-loaded autologous DCs but without activated allogeneic cells (d, e and f) and expansion with activated allogeneic cells with unloaded autologous DCs (g, h and i).

Results: The results are shown in FIG. 10 and the table 1 below.

The frequency of virus-specific CD8 positive cells (specific for CMV, EBV or influenza A virus respectively) increases after expansion with activated allogeneic cells and incubation in a control culture without activated allogeneic cells. As can be seen in FIG. 10

TABLE 1

Shows the frequency of virus-specific cells (expressed as IFN-γ-spots per $10^6$ cells) after expansion with activated allogeneic PBMC.

| Experiment | IFN-γ-producing (cells/$10^6$) (ELISPOT) |
|---|---|
| CMV-specific cells expanded with activated allogeneic PBMC and restimulated with pulsed DC | >5000 |
| CMV-specific cells expanded without activated allogeneic PBMC and restimulated with pulsed DC | 250 |
| Non-virus-specific cells expanded with activated allogeneic PBMC and restimulated with pulsed DC | 60* |

*Only DC gives a background of 68 cells/$10^6$

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

The invention claimed is:

1. An in vitro method for priming of antigen specific CD4+ and/or CD8+ T cells for administration to a patient having a viral infection, said method comprising co-culturing (1) target T cells from the patient to be treated, (2) mature monocyte-derived dendritic cells from a first healthy donor, (3) virus material or virus associated proteins or peptides, and (4) lymphocytes from a second healthy donor sensitized against MHC class I and/or MHC class II antigens on antigen presenting cells (APCs) from the first healthy donor that are allogeneic with respect to the lymphocytes, wherein the lymphocytes are obtained by culturing non-proliferating peripheral blood mononuclear cells (PBMCs) from the first healthy donor with PBMCs from the second healthy donor.

2. The method according to claim 1, wherein the non-proliferating PBMCs are inactivated by irradiation.

3. The method according to claim 1, wherein the mature monocyte-derived dendritic cells are obtained by first culturing monocytes in a composition comprising GM-CSF and IL-4 for about 1-7 days to obtain immature dendritic cells and subsequently adding a second composition that enables the immature dendritic cells to become mature dendritic cells by culturing for at least about 12 hours.

4. The method according to claim 3, wherein the second composition comprises TNF alfa, IL-1 beta, interferon gamma, interferon alpha or beta and a TLR3 ligand and/or a TLR 4 ligand.

5. The method according to claim 3, wherein the second composition comprises TNF alfa, interferon gamma, a TLR 3 and/or a TLR 4 ligand and a TLR7 and/or a TLR 8 agonist.

6. The method according to claim 5, wherein the TLR 3 ligand is poly-1:C and the TLR 8 agonist is R848.

7. The method of claim 1, wherein the, viral material or virus associated proteins or peptides are selected from the group consisting of killed virus particles from the patient, allogeneic virus particles of the same type as the virus of the patient and known isolated and purified virus proteins or peptides.

8. The method according to claim 7, wherein the virus material is virus proteins loaded into the mature dendritic cells by transfection with mRNA encoding the virus protein.

9. The method according to claim 1, wherein the T cells are cultured for at least about 20 days.

10. The method according to claim 1, wherein anti-CD3 antibodies and/or exogenous IL-2, IL-7, IL-15, anti-IL-4 and/or IL-21 are added to the cell culture.

11. The method according to claim 1, wherein the primed antigen specific CD4+ and/or CD8+ T cells are restimulated by culturing said cells together with new dendritic cells, new sensitized lymphocytes and optionally addition of anti-CD3 antibodies and/or exogenous IL-2, IL-7, IL-15, anti-IL-4 and/or IL-21 to the cell culture.

12. The method according to claim 1, wherein the viral infection is a chronic viral infection.

13. The method according to claim 12 wherein the chronic viral infection is selected from the group consisting of HIV, HBV, HCV, CMV and EBV.

14. The method according to claim 4, wherein the TLR3 ligand is poly-1:C.

15. The method according to claim 1, wherein the T cells are cultured for about 6 to 20 days.

16. The method according to claim 1, wherein the T cells are cultured for about 8 to 14 days.

* * * * *